(12) United States Patent
Verleye et al.

(10) Patent No.: US 9,872,858 B2
(45) Date of Patent: Jan. 23, 2018

(54) TREATMENT OF DEGENERATIONS AND LIGHT-INDUCED DAMAGE TO THE RETINA

(71) Applicant: BIOCODEX, Gentilly (FR)

(72) Inventors: Marc Verleye, Remy (FR); Philippe Girard, Margny les Compiegne (FR); Marie-Emmanuelle Le Guern, Compiegne (FR)

(73) Assignee: BIOCODEX, Gentilly (FR)

( * ) Notice: Subject to any disclaimer, the term of this patent is extended or adjusted under 35 U.S.C. 154(b) by 0 days.

(21) Appl. No.: 15/115,089

(22) PCT Filed: Jan. 28, 2015

(86) PCT No.: PCT/EP2015/051669
§ 371 (c)(1),
(2) Date: Jul. 28, 2016

(87) PCT Pub. No.: WO2015/113991
PCT Pub. Date: Aug. 6, 2015

(65) Prior Publication Data
US 2017/0000798 A1    Jan. 5, 2017

(30) Foreign Application Priority Data
Jan. 29, 2014   (FR) ..................... 14 00223

(51) Int. Cl.
| A61K 31/536 | (2006.01) |
| A61K 31/517 | (2006.01) |
| A61K 31/573 | (2006.01) |
| A61K 45/06 | (2006.01) |

(52) U.S. Cl.
CPC .......... *A61K 31/536* (2013.01); *A61K 31/517* (2013.01); *A61K 31/573* (2013.01); *A61K 45/06* (2013.01)

(58) Field of Classification Search
CPC .. A61K 31/536; A61K 31/517; A61K 31/573; A61K 45/06
See application file for complete search history.

(56) References Cited

U.S. PATENT DOCUMENTS

2004/0102438 A1    5/2004  Brueckner et al.
2006/0292202 A1    12/2006  Bartels

FOREIGN PATENT DOCUMENTS

WO   WO-2007109288   9/2007
WO   WO-2014025792   2/2014

OTHER PUBLICATIONS

Marc Verleye et al: "Effects of etifoxine on ligand binding to GABAA receptors in rodents", Neuroscience Research, Elsevier, Shannon, IR, vol. 44, Jan. 1, 2002 (Jan. 1, 2002), pp. 167-172, XP007908404, ISSN: 0168-0102, DOI: 10.1016/S0168-0102(02)00121-9 p. 167.
International Search Report for PCT/EP2015/051669, dated Apr. 21, 2015.
Written Opinion for the International Searching Authority for PCT/EP2015/051669, dated Apr. 21, 2015.

*Primary Examiner* — Kahsay Habte
(74) *Attorney, Agent, or Firm* — B. Aaron Schulman, Esq.; Stites & Harbison, PLLC.

(57) ABSTRACT

The present invention relates to a compound of the following formula (I):

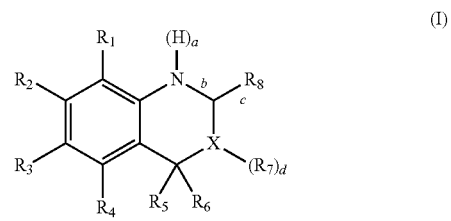

or a pharmaceutically acceptable salt thereof, to be used in the prevention or treatment of light-induced damage and/or a degeneration of the retina in a patient.

13 Claims, 2 Drawing Sheets

TREATMENT OF DEGENERATIONS AND LIGHT-INDUCED DAMAGE TO THE RETINA

FIELD OF THE INVENTION

The present invention relates to compounds and pharmaceutical compositions useful for the prevention or treatment of retinal degenerations and/or light-induced damages of the retina, and in particular for the prevention or the treatment of age-related macular degeneration (AMD).

BACKGROUND OF THE INVENTION

Retinal degenerations and light-induced damages of the retina include diseases such as photoretinitis, retinitis pigmentosa, age-related maculopathy (ARM) and age-related macular degeneration (AMD).

Among these diseases, AMD is particularly important since it represents the leading cause of vision loss after 55 years of age in industrialized countries. The global prevalence of the disease is 8% after 50 and increases with age, from about 1 to 2% between 50 and 65, to 10% between 65 and 75, then to 25% between 75 and 85.

The etiology of AMD is unknown but several risk factors have been identified or are suspected, including age, smoking habits, arterial hypertension, the light color of the iris, antecedents of coronary events, and significant exposure to light. In addition, genetic factors also play a role in the onset of the disease.

There are several stages in AMD: early stages, which correspond to age-related maculopathy (ARM), as well as later stages, corresponding to AMD in the strict sense, which include non-exudative forms, also called dry forms, or atrophic forms in their advanced stage, and exudative forms, also called wet or neovascular forms.

In France, there is, at present, no drug treatment approved for the treatment of atrophic AMD. As for the exudative form of AMD, anti-VEGFs (Vascular Endothelial Growth Factor) administered by the intravitreal route are the only first-line treatment recommended by the High Authority of Health (HAS). It has thus been shown that ranibizumab, a Fab fragment of an anti-VEGF-A monoclonal antibody, monthly administered by intravitreal injections of 0.3 mg and 0.5 mg allows a visual acuity improvement of +8.1 and +10.7 letters respectively in patients suffering from neovascular (exudative) AMD, while a loss of visual acuity of 9.8 letters was observed in control patients treated with dynamic phototherapy (for review see Fong & Lai (2013) *Clinical Interventions in Aging* 8:467-483).

Accordingly, there is an unmet need in regard of the pharmacological management of the non-exudative form, in particular the atrophic form, of AMD. Furthermore, as for the exudative form, it would be useful to have a treatment for limiting, or even stopping, the use of intravitreal injections that are particularly uncomfortable for the patient.

In this context, given the protective action of phenyl-N-tert-butyl-nitrone in light-induced degeneration of the retina in rats after intraperitoneal injection (Ranchon et al. (2001) *Investigative Ophthalmology & Visual Science* 42:1375-1379), it has been proposed to use it in AMD treatment, in particular for its dry form. However, no clinical trials have been performed for this compound that could lead to its use in humans.

Etifoxine or 6-chloro-2-ethylamino-4-methyl-4-phenyl-4H-[3,1]benzoxazine hydrochloride belongs to the family of aminobenzoxazines. It promotes GABA transmission by binding to a site near the chloride channel coupled to $GABA_A$ receptor and is currently used as an anxiolytic. Few adverse events following its use are listed.

Etifoxine

The synthesis of this compound is described in French patent n°1 571 287. Moreover, several active metabolites of etifoxine have been described, such as desethyl-etifoxine or 2-amino-6-chloro-4-methyl-4-phenyl-4H-[3,1]benzoxazine, 6-chloro-4-(4-hydroxyphenyl)-4-methyl-3,4-dihydro-1H-quinazolin-2-one or 6-chloro-3-ethyl-7-hydroxy-4-methyl-4-phenyl-3,4-dihydro-1H-quinazolin-2-one.

SUMMARY OF THE INVENTION

The present invention follows from the unexpected finding that etifoxine protects the retina of animals subjected to light irradiation inducing retinal damages, which notably model AMD.

Thus, the present invention relates to a compound of the following formula (I):

wherein:
a represents 0 or 1,
b represents a single bond or a double bond,
c represents a single bond or a double bond,
d represents 0 or 1,
X represents an oxygen or nitrogen atom, provided that when X represents an oxygen atom then d has the value of 0 and when X represents a nitrogen atom then d has the value of 1,
$R_1$, $R_2$, $R_3$, and $R_4$, which are the same or different, represent a hydrogen atom, a halogen atom, in particular selected from F, Cl, Br, or I, a hydroxyl group, or an alkoxyl group having 1 or 2 carbon atoms,
$R_5$ and $R_6$, which are the same or different, represent a hydrogen atom, an alkyl or cycloalkyl group having from 1 to 6 carbon atoms, or an aryl group having 6 carbon atoms in which the aromatic ring may be substituted by one or more halogen atoms or one or more hydroxyl groups, alkoxyl groups having 1 or 2 carbon atoms, trifluoromethyl groups or nitro groups,
$R_7$ represents a hydrogen atom, a hydroxyl group, or an alkyl or hydroxyalkyl group having from 1 to 3 carbon atoms, $R_8$ represents an oxygen atom or a —$NR_9R_{10}$ group, $R_9$ and $R_{10}$, which are the same or different, representing a hydrogen atom, a hydroxyl group, or an alkyl or hydroxyalkyl group having from 1 to 3 carbon atoms, provided than when $R_8$ represents an oxygen atom then a has the value 1, b represents a single bond and c represents a double bond and that when $R_8$ represents a —$NR_9R_{10}$ group then a has the value 0, b represents a double bond and c represents a single bond, or pharmaceutically acceptable salt thereof, for its use in the prevention or treatment of a light-induced damage and/or degeneration of the retina in an individual.

In a particular embodiment of the invention, the compound or the pharmaceutically acceptable salt thereof, for its use as defined above, is in combination with at least one additional compound useful for preventing or treating a light-induced damage and/or a degeneration of the retina. In another particular embodiment of the invention, the compound or the pharmaceutically acceptable salt thereof for its use as defined above is not in combination with at least one additional compound useful for preventing or treating a light-induced damage and/or degeneration of the retina.

The present invention also relates to a pharmaceutical composition comprising as active ingredient at least one compound of formula (I) as defined above, or a pharmaceutically acceptable salt thereof, optionally in association with a pharmaceutically acceptable vehicle, for its use in the prevention or treatment of a light-induced damage and/or retinal degeneration of the retina in an individual.

In a particular embodiment of the invention, the pharmaceutical composition for its use as defined above comprises at least one additional compound useful for the prevention or treatment of a light-induced damage and/or a degeneration of the retina. In another particular embodiment of the invention, the pharmaceutical composition for its use as defined above does not include another compound useful for the prevention or treatment of a light-induced damage and/or a degeneration of the retina.

The present invention also relates to a pharmaceutical composition comprising as active ingredients at least one compound of formula (I) as defined above, or a pharmaceutically acceptable salt thereof, and at least one additional compound useful for the prevention or treatment of a light-induced damage and/or a degeneration of the retina, optionally in association with a pharmaceutically acceptable vehicle.

The present invention also relates to products containing:
at least one compound of formula (I) as defined above, or a pharmaceutically acceptable salt thereof, and
at least one additional compound useful for the prevention or treatment of a light-induced damage and/or degeneration of the retina, as product combined preparation for use, in particular for simultaneous, separated or sequential use, in the prevention or treatment of a light-induced and/or degeneration of the retina in an individual.

The present invention also relates to a method for the prevention or treatment of a light-induced damage or a degeneration of the retina in an individual, comprising administering the individual an effective quantity of a compound of formula (I) as defined. above, or of a pharmaceutically acceptable salt thereof.

In a particular embodiment of the invention, the method as defined above also comprises the administration of at least one additional compound useful for the prevention or treatment of a light-induced damage and/or a degeneration of the retina to the individual.

The present invention also relates to the use of a compound of formula (I) as defined above, or a pharmaceutically acceptable salt thereof, for the manufacture of a medicament intended for the prevention or treatment of a light-induced damage and/or a degeneration of the retina in an individual.

In a particular embodiment of the invention, the medicament as defined above comprises at least one additional compound useful for the prevention or treatment of a light-induced damage and/or a degeneration of the retina.

DETAILED DESCRIPTION OF THE INVENTION

Degeneration or Light-Induced Damage of the Retina

The invention relates to the prevention or treatment of any degeneration of the retina and/or light-induced damage of the retina, in particular by preserving or restoring the function of the retinal photoreceptors.

Preferably, the degenerations and light-induced damages of the retina according to the invention are selected from the group consisting of photoretinitis, retinitis pigmentosa, age-related maculopathy (ARM), or age-related macular degeneration (AMD). More preferably, the light-induced damage and/or the degeneration of the retina according to the invention, is AMD, more particularly in a moderate or advanced stage, especially in its non-exudative form, also called dry, or atrophic form.

These diseases are well known by the person skilled in the art.

Photoretinitis is a retinal damage induced by light, in particular called "blue" light, comprising at least one component having a wavelength between 400 nm and 550 nm.

Retinitis pigmentosa, also called pigmentary retinopathy, is an inherited dystrophy of the retina involving a degeneration of the retina associated with the loss of photoreceptors, cones and/or rods, and characterized by visible pigment deposits in the fundus of the eye. Retinitis pigmentosa within the meaning of the invention can be non-syndromic or syndromic, that is to say associated with a damage of other organs. Thus, retinitis pigmentosa within the meaning of the invention also covers syndromes such as Usher's syndrome, Bardet-Biedl's syndrome and Refsum's disease.

Age-related maculopathy (ARM) associates one or more of the following elements together:
Miliary drusen: asymptomatic small white spots observed in the perimacular region (less than 63 μm of diameter);
Serous drusen: larger drusen (more than 125 μm), usually asymptomatic but may be associated with a decrease of visual capabilities in the dark;
Pigmentary changes such as hypopigmentation or hyperpigmentation of the pigment epithelium. They reflect cell deaths of the pigmentary epithelium.

AMD according to the invention presents under two forms, exudative AMD, also called wet form, and non-exudative AMD, also called dry form, or atrophic form in a late stage.

Exudative AMD is characterized by the proliferation of choroidal neovessels which cross Bruch's membrane and develop under the pigment epithelium or within the subretinal space. There are particular forms of neovessels in exudative AMD, including:
Chorioretinal anastomosis, also called type 3 neovascularization;
Idiopathic polypoidal vasculopathy.

Polypoidal vasculopathies, which are related to the development of an abnormal vascular network of choroidal origin that develops under the retinal pigment epithelium, ending with polypoi dal dilatations; these damages cause sero-hemorrhagic retinal detachment and pigment epithelium detachment preferentially localized in the inter-papillo-macular area.

Atrophic AMD or geographic atrophy is the advanced form of non-exudative AMD and is characterized by one or more ranges of atrophy of the pigment epithelium and/or the choriocapillaris membrane that are observed more or less associated with drusen (accumulation of lipid deposits under the pigment epithelium and within Bruch's membrane) and abnormalities of the pigment epithelium. Atrophy can also be associated with neovascul an zation.

AMD according to the invention can also be classified into four stages or categories defined by the AREDS (Age-Related Eye Disease Study):

| | |
|---|---|
| Category 1 | No age-related macular degeneration: no or few small drusen (less than 63 μm of diameter) |
| Category 2: ARM | One or more of the following elements: multiple small drusen; some drusen with a diameter between 63 et 125 μm; abnormal pigment epithelium. |
| Category 3: moderate AMD | One or more of the following elements: some drusen with a diameter between 63 and 125 μm and at least one drusen with a diameter larger than 125 μm; geographic atrophy excluding the fovea |
| Category 4: advanced AMD | Geographic atrophy affecting the fovea and/or presence of an exudative age-related macular degeneration |

Thus, particularly preferably, the light-induced damage and/or the degeneration of the retina according to the invention is a category 3 or 4 non-exudative AMD according to the AREDS classification, that is to say a moderate or advanced non-exudative AMD.

Individual

The individual within the meaning of the invention is preferably a human, more preferably aged 50 or more.

In a preferred embodiment of the invention, the individual according to the invention follows a photodynamic therapy. Photodynamic therapy is well known by the person skilled in the art; it combines a laser radiation of low intensity after the injection of a sensitizing product, in particular verteporfin, which electively attaches itself to the wall of neovessels.

When the invention aims at treating a light-induced damage or a degeneration of the retina it is preferable that the individual suffers from an ARM, a moderate or category 3 AMD, or an advanced or category 4 AMD, especially from an advanced or category 4 AMD, in particular in its non-exudative form.

Besides, When the invention aims at preventing a light-induced damage or a degeneration of the retina it is preferred that the individual has a five year-risk score of progression from an early form of AMD to an advanced form of at least 1, more preferably at least 2, even more preferably at least 3, and most preferably at least 4.

As is well known by the person skilled in the art and as it is in particular described in the publication "Age-related Macular degeneration: patient support, diagnosis and therapy" of June 2012 from the National Health Authority (HAS) (France), the risk assessment of progression from an early form of AMD to an advanced form in five years is provided as a score from 0 to 4 based on the abnormalities present in one or both eyes:

A score of 1 is assigned per eye when large drusen or pigmentary anomalies are present.
The score is 2 if the two elements are present (presence of large or pigmentary anomalies).
A score of 2 is assigned to an eye with an advanced AMD (geographic atrophy affecting the fovea and/or presence of an exudative AMD).
The score of each eye is added and corresponds to a risk level. The resulting score is then correlated with a risk percentage to develop an advanced AMD within five years:
a score of 0 corresponds to a risk of 0.5%;
a score of 1 corresponds to a risk of 3%;
a score of 2 corresponds to a risk of 12%;
a score of 3 corresponds to a risk of 25%;
a score of 4 corresponds to a risk of 50%.

Compound of Formula (I)

The synthesis of compounds of formula (I) as defined above can easily be implemented from the teachings of French Patent No. 1,571,287.

Pharmaceutically acceptable salts according to the invention will be obvious to those skilled in the art. In particular, the hydrochloride salts of the compounds of formula (I) according to the invention are preferred.

As intended herein, the above-defined formula (I) in particular includes the formulae of the optically active compounds of formula (I), such as the enantiomers represented by the following formulae (when $R_5$ and $R_6$ are different):

or their mixtures, in particular their racemic mixture.

In a preferred embodiment of the invention, in the above-defined formula (I), $R_5$ and $R_6$, which are the same or different, represent an alkyl or cycloalkyl group from 1 to 6 carbon atoms, or an aryl group of 6 carbon atoms, in which the aromatic ring may be substituted by one or more halogen atoms or one or more hydroxyl groups, alkoxyl groups having 1 or 2 carbon atoms, trifluoromethyl groups or nitro groups.

In a preferred embodiment of the invention, the above-defined formula (I) is represented by the following formula (VIII):

(VIII)

wherein:
a represents 0 or 1,
b represents a single bond or a double bond,
c represents a single bond or a double bond,
d represents 0 or 1,

X represents an oxygen or nitrogen atom, provided that that when X represents an oxygen atom then d has the value 0 and when X represents a nitrogen atom then d has the value 1, $R_{11}$ and $R_{12}$, which are the same or different, represent —H or —OH, $R_{13}$ represents —H or a —CH$_2$—CH$_3$ group,

$R_{14}$ represents an oxygen atom or a —NH$_2$ or —NH—CH$_2$—CH$_3$ group, provided that when $R_{14}$ represents an oxygen atom then a has the value of 1, b represents a single bond and c represents a double bond and that when $R_{14}$ represents a —NH$_2$ or —NH—CH$_2$—CH$_3$ group then a has the value of 0, b represents a double bond and c represents a single bond.

As intended herein, the above-defined formula (VIII) in particular includes the formulae of the optically active compounds of formula (VIII), such as the g enantiomers represented by the following formulae:

or their mixtures, in particular their racemic mixture.

In another preferred embodiment of the invention, the above-defined formula (I) is represented by the following formula (II):

wherein $R_1$, $R_2$, $R_3$, $R_4$, $R_5$, $R_6$, $R_9$ and $R_{10}$ are as defined above.

As intended herein, the above-defined formula (II) in particular includes the formulae of the optically active compounds of formula (II), such as the enantiomers represented by the following formulae (when $R_5$ and $R_6$ are different):

or their mixtures, in particular their racemic mixture.

In another preferred embodiment of the invention, the above-defined formula (I) is represented by the following formula (IIIa), (IIIb) or (IV):

The compound of formula (IIIa) is base etifoxine or 6-chloro-2-ethylamino-4-methyl-4-phenyl-4H-[3,1]benzoxazine. The compound of formula (IIIb) is etifoxine, or 6-chloro-2-ethylamino-4-methyl-4-phenyl-4H-[3,1]benzoxazine hydrochloride.

The compound of formula (IV), desethyl-etifoxine or 2-amino-6-chloro-4-methyl-4-phenyl-4H-[3,1]benzoxazine, is a metabolite of etifoxine.

As intended herein, the above-defined formula (IIIa) or (IIIb) in particular includes the formulae of the optically active compounds of formula (IIIa) or (IIIb), such as the enantiomers represented by the following formulae:

or their mixtures, in particular their racemic mixture, in particular in the form of hydrochloride, as well as the formulae of the optically activecompounds of formula (IV), such as the enantiomers represented by the following formulae:

or their mixtures, in particular their racemic mixture.

In another preferred embodiment of the invention, formula (I) is represented by the following formula (V):

wherein $R_1$, $R_2$, $R_3$, $R_5$, $R_6$, and $R_7$ are as defined above.

As intended herein, the above-defined formula (V) in particular includes the formulae of the optically active compounds of formula (V), such as the enantiomers represented by the following formulae (when $R_5$ and $R_6$ are different):

or their mixtures, in particular their racemic mixture.

In another preferred embodiment of the invention, formula (I) is represented by the following formula (VI) or (VII):

The compounds of formulae (VI) (6-chloro-4-(4-hydroxy-phenyl)-4-methyl-3,4-dihydro-1H-quinazolin-2-one) and (VII) (6-chloro-3-ethyl-7-hydroxy-4-methyl-4-phenyl-3,4-dihydro-1H-quinazolin-2-one) are metabolites of etifoxine.

As intended herein, the above-defined formula (VI) in particular includes the formulae of the optically active compounds of formula (VI), such as the enantiomers represented by the following formulae:

or their mixtures, in particular their racemic mixture, as well as the formulae of the optically active compounds of formula (VII), such as the following enantiomers:

or their mixtures, in particular their racemic mixture.

Additional Compound

The other compound useful for the prevention or treatment of a light-induced damage and/or a degeneration of the retina according to the invention can be of any type, however it is preferably selected from the group constituted of an anti-VEGF, a corticoid and an antioxidant.

Anti-VECiFs are well known by the person skilled in the art, they are generally iligands of isoform A of VEGF, which include, in particular, ranibizumab, pegaptanib, bevacizumab and aflibercept.

Corticoids according to the invention are preferably triamcinolone and anecortave acetate.

Antioxidants according to the invention are preferably anthocyanosides, β-carotene and α-tocopherol.

Administration

Preferably, the compound of formula (I) as defined above, or its pharmaceutically acceptable salt, is administered or administrable at a unit dose, or is packaged in a unit dose, of about 50 mg to about 1500 mg, in particular from about 150 to about 200 mg. Preferably also, the compound of formula (I) as defined above, or its pharmaceutically acceptable salt is administered or administrable at a dosage regimen of 50 mg/day to about 1500 mg/day, in particular from about 150 mg/day to about 200 mg/day.

Preferably, the compound of formula (I) as defined above, or its pharmaceutically acceptable salt is administered or administrable in a form suitable for administration by the oral or injectable route. More preferably, the compound of formula (I) as defined above, or its pharmaceutically acceptable salt, is administered or administrable in the form of a powder, tablets, capsules or sachets. Preferably, the compound of formula (I) as defined above, or its pharmaceutically acceptable salt, is not included in a reservoir of a hydrogel matrix for administration to the eve surface of an individual.

As understood here, the expression "in combination" or "combined preparation" means that the compound of formula (I) as defined above, or its pharmaceutically acceptable salt, and the other compound useful for the prevention or treatment of a light-induced damage and/or a degeneration of the retina as defined above may he associated within the same pharmaceutical composition or the same medicament, and therefore be administered together, or may be administered separately, that is to say by separated routes of administration and/or separated administration regimens, provided that when they are administered separately, the periods of the compound of formula (I) as defined above and of the other compound useful for the prevention or treatment of a light-induced damage and/or a degeneration of the retina as defined above overlap entirely or partially.

Thus, when the compounds are administered separately, the compound of formula (I) as defined above, or its pharmaceutically acceptable salt will preferably be administered within 24 hours, more preferably within 2 hours, and even more preferably in the hour following the administration of the other compound useful for the prevention or treatment of a light-induced damage and/or a degeneration of the retina as defined above, and its administration may continue the following days. Reciprocally, the other compound useful for the prevention or treatment of a light-induced damage andlor a degeneration of the retina as defined above will preferably be administered within 24 hours, more preferably within 2 hours, and even more preferably in the hour following the administration of the compound of formula (I) as defined above, or its pharmaceutically acceptable salt, and its administration may continue the following days. In another preferred embodiment of the invention, when the compound of formula (I) as defined above and the other compound useful for the prevention or treatment of a light-induced damage andlor a degeneration of the retina as defined above are administered separately, they are administered essentially simultaneously.

The invention is further described in the following. non-limiting Example and Figures.

DESCRIPTION OF THE FIGURES

FIG. 2 shows the average thickness of the outer nuclear layer 14 days after the induction of retinal degeneration (y-axis, in μm) as a function of the distance to the optic nerve (x-axis, in mm). The dark gray/square dots/solid line curve represents the group of rats treated with etifoxine at 12.5 mg/kg, the light gray/square dots/solid line curve represents the group of rats treated with etifoxine at 25 mg/kg, the medium gray/square dots/solid line curve represents the group of rats treated with etifoxine at 50 mg/kg, the light gray/round dots/dashed line curve represents the group of rats treated with the vehicle, the light gray/triangular dots/dashed line curve represents the group of rats treated with PBN at 50 mg/kg and the light gray/diamond dots/dotted line curve represents the group of rats treated with a solution of NaCl 0.9%.

EXAMPLE

The inventors have studied the protective effect of etifoxine in respect of the blue light-induced retinal degenerations or damages in rats. This animal model is particularly representative, in addition to light-induced retinal damage, of age-related macular degeneration (AMD) and retinitis pigmentosa (see e.g Feng et al. (2012) *International Journal of Ophthalmology* 5:151-157).

I. Material and methods
I.1. Products

The Tween 80 used as vehicle of etifoxine, was obtained from Sigma and diluted to 1% (v/v) in a sterile solution of 0.9% NaCl (Supplier: Aguettant). Etifoxine (6-chloro-2-ethylamino-4 -methyl-4-phenyl-4H-[3,1]benzoxazine hydrochloride) (hereinafter also referred to as EFX) was obtained in a powder form from Biocodex. Less than 6 hours prior to administration, etifoxin.e is suspended in the 1% of Tween 80 vehicle solution at concentrations of 2.5 mg/mL, 5 mg/ml and 10 mg/mL and stored at 2° C. to 8° C.

Phenyl-N-tert-butylnitrone (PBN) (reference product) was obtained in a powder form from Sigma. Less than 12 hours prior to administration, PBN is dissolved in a sterile saline solution of 0.9% NaCl at a concentration of 20 mg/mL and is protected from light during storage at a temperature between 2° C. and 8° C.

I.2. Animals

The animals used were treated in accordance with Directive 2010/63/EU and the recommendations of the Association for Research in Vision and Ophthalmology (ARVO).

72 Sprague-Dawley albino male rats obtained from Janvier were used for the study. When received, the rats were approximately 7 weeks old and weighed 180-200 g, The rats were kept under observation for 3 weeks after their arrival for acclimatization. Meanwhile the animals were observed daily for verifying the absence of a disease. The animals included in the study were free of ocular abnormalities.

Outside induction (exposure to blue light), the animals were kept in groups of 2 or 3 in standard cages under identical environmental conditions: temperature at 22±2° C.; humidity at 55±10%; day cycle (10-200 lx)—night of 12 h/12 h. The animals had free access to water (tap water) and food (LASvendi GmbH).

I 1.3. Experimental Procedure

The 72 rats were divided into 6 groups of 12 animals and were subjected to the treatments summarized in the following table:

| Group | Treatment | Dose | Administration route | Dosage regimen |
|---|---|---|---|---|
| 1 | Etifoxine | 12.5 mg/kg | Intraperitoneal | Once a day from D-7 to D0 30 min. before induction at D0 |
| 2 | (EFX) | 25 mg/kg | 0.5 mL/100 g | |
| 3 | | 50 mg/kg | | |
| 4 | Vehicle | — | | |
| 5 | NaCl 0.9% | — | Intraperitoneal 0.25 mL/100 g | At D0, 0.5 h before induction, at 2 h et 4 h during the induction and just after induction |
| 6 | PBN | 50 mg/kg | | |

Induction was performed by exposure during 6 hours to a blue fluorescent light of 400 nm-540 nm wavelength in individual cages. The rats were kept in the dark for 36 hours prior to the induction and 24 hours after the induction, before returning to normal lighting conditions.

A scotopic electroretinogram (ERG) was performed by using the electrophysiological RETI-animal® (Roland Consult) system before the first administration (base) then on days 7 and 14 on both eyes of animals accustomed to the darkness. The animals were anesthetized with an intramuscular injection of a mixture of ketamine/xylazine. 15 minutes before the measurement, 1 drop of Mydriatictum® (0.5% tropicamide) was instilled to induce dilatation of the pupil. The amplitudes of wave a and wave b were measured for each eye and expressed as a percentage of the base amplitudes.

The ERG parameters are:
Gansfeld Q450C
Color: maximum white
Maximum intensity: 2.6 cd.s/m$^2$ (0 dB); duration: 0.24 ms; number of flashes: 1
Filter: 50 Hz
Impedance threshold: 90 kΩ

After ERG (day 14), the animals were euthanized with an overdose of pentobarbital, according to European recommendations, both eyes were enucleated, fixed with Bouin Hollande solution and then included in paraffin. Sections of 5 to 7 μm of thickness were made along the vertical meridian then stained using Masson's trichrome. The vertical meridian includes the optic nerve. The thickness of the outer nuclear layer (ONL) was determined every 500 μm, for seven points, from the optic nerve, towards the peripheral retina, both in the superior retina and the inferior retina, with a standard microscope (Leica). The area under the curve (AUC) was then calculated for each retina.

Statistical analyses were performed using GraphPad Prism 6.0 software.

A two-factor ANOVA test was applied to the average amplitudes of the wave a of both eyes for each measurement point. The effect of the products was determined using the Turkey's multiple comparison test; each group was compared to other groups. Differences were considered significant for p values less than 0.05.

A one-factor ANOVA test was applied to the average AUCs of the thickness of the outer nuclear layer. The effect of the products was determined using a Turkey's multiple comparison test; each treated group was compared to vehicle group. Differences were considered significant for p values less than 0.05.

II. Results

II.1. Animals Behavior and Body Weight

No unexpected clinical signs were recorded after the administration of etifoxine.

No significant difference of weight gain was found between the different groups of rats.

II.2. Electroretinograms

Electroretinograms (ERG) allow to measure the amplitude of wave a, which results from the photo-activated hyperpolarization of photoreceptors. Thus, a reduction of the amplitude of wave a is an indicator of a retinal damage or degeneration associated with exposure to blue light.

Figure 1:
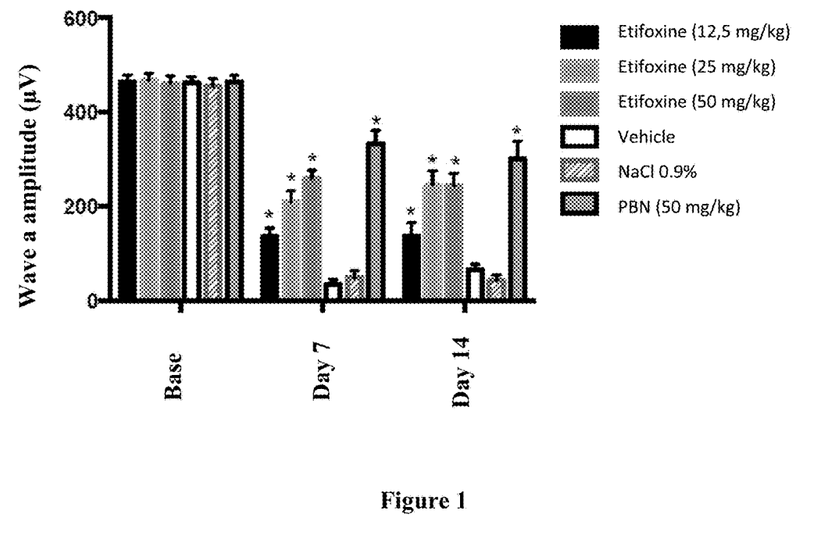
FIG. 1 shows the average amplitude of wave a (Y-axis, in μV) before the induction of retinal degeneration (base), 7 days after induction and 14 days after induction for groups of rats treated with etifoxine administered at 12.5 mg/kg (black bars), 25 mg/kg (light gray bars), 50 mg/kg (dark gray bars), or with vehicle alone (white bars), with a 0.9% NaCl solution (hatched bars) or PBN (gray bars surrounded by black). The star symbol (*) represents $p<0.05$ compared to vehicle group or NaCl 0.9%.

The amplitudes of wave a of both eyes were averaged for each rat and mean values are shown in FIG. 1 and Table 1:

TABLE 1

| | amplitude and relative amplitude of wave a | | | | |
|---|---|---|---|---|---|
| | Base | Day 7 | | Day 14 | |
| Treatment | Amplitude of wave a (μV, mean ± standard deviation) | Amplitude of wave a (μV, mean ± standard deviation) | Average relative amplitude of wave a (%) | Amplitude of wave a (μV, mean ± standard deviation) | Average relative amplitude of wave a (%) |
| EFX 12.5 mg/kg | 465 ± 68 | 136 ± 89 | 32 ± 23 | 134 ± 135 | 33 ± 36 |
| EFX 25 mg/kg | 468 ± 70 | 210 ± 116 | 45 ± 24 | 245 ± 143 | 53 ± 31 |
| EFX 50 mg/kg | 461 ± 82 | 260 ± 87 | 59 ± 21 | 244 ± 138 | 52 ± 26 |

TABLE 1-continued

| | amplitude and relative amplitude of wave a | | | | |
|---|---|---|---|---|---|
| | Base | Day 7 | | Day 14 | |
| Treatment | Amplitude of wave a (µV, mean ± standard deviation) | Amplitude of wave a (µV, mean ± standard deviation) | Average relative amplitude of wave a (%) | Amplitude of wave a (µV, mean ± standard deviation) | Average relative amplitude of wave a (%) |
| Véhicule | 463 ± 64 | 35 ± 53 | 8 ± 13 | 66 ± 58 | 15 ± 14 |
| NaCl 0.9% | 455 ± 78 | 50 ± 68 | 10 ± 12 | 44 ± 55 | 9 ± 11 |
| PBN 50 mg/kg | 465 ± 67 | 334 ± 137 | 71 ± 29 | 301 ± 187 | 62 ± 38 |

N.B.: relative amplitude is a percentage of base amplitude

The amplitude of wave a is significantly reduced ($p<0.0001$) to 8 to 15% of basal levels 7 and 14 days after exposure for the vehicle groups and 0.9% NaCl (negative controls), which validates induction. Besides, animals treated with the reference product PBN (positive controls) show amplitudes of the wave a significantly ($p<0.0001$) higher than those of the NaCl 0.9% group, at days 7 and 14, which validates the treatment procedure.

Regarding treatments with etifoxine, a significant dose-dependent protection was observed from 7 days after induction ($p<0.0001$ for all doses compared to the vehicle group), and also 14 days after the induction ($p=0,016$ for 12.5 mg/kg and $p<0.0001$ for 25 and 50 mg/kg compared to the vehicle group).

II.3. Measurement of the Thickness of the Outer Nuclear Layer

To determine if the treatment allows to preserve the structure of photoreceptors, the thickness of the outer nuclear layer was evaluated 14 days other exposure to blue light. The area under the curve (AUC) of the thickness of the outer nuclear layer was calculated for each eye and both AUCs were averaged for each rat.

Figure 2:
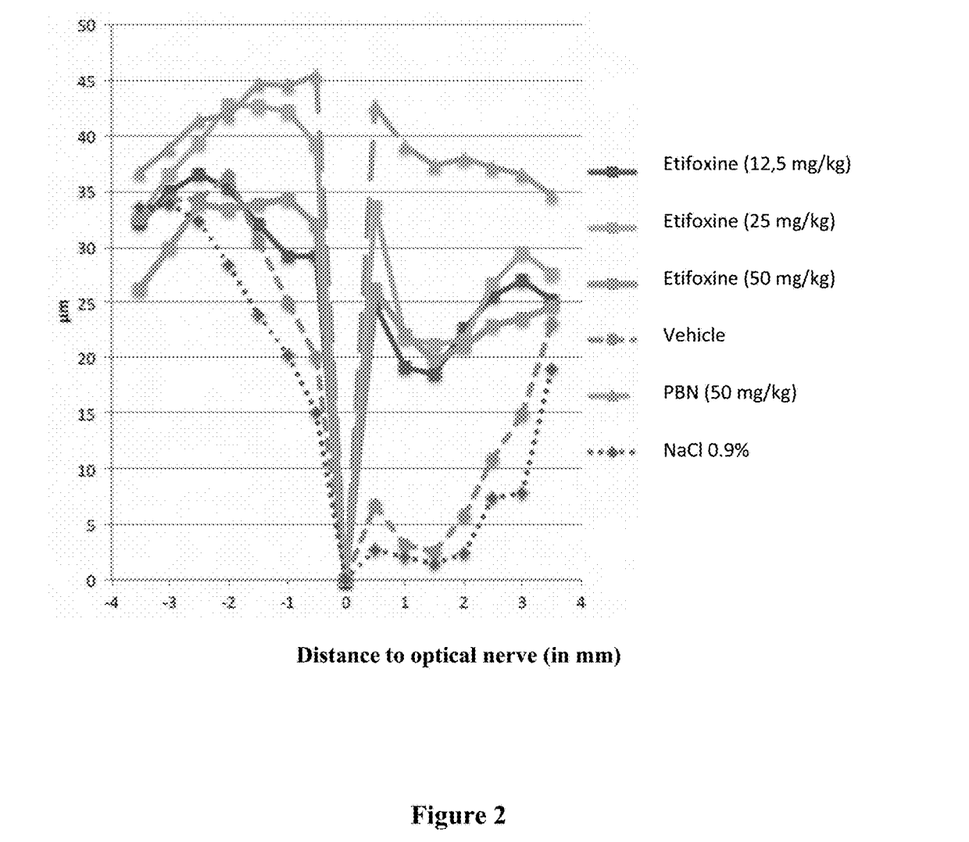

FIG. 2 illustrates the average thickness of the outer nuclear layer along the retina. Besides, the integration of the area under the curve representing the thickness of the outer nuclear layer was calculated to compare different treated groups. The mean of both eyes of the AUC thus calculated is shown in Table 2 below:

TABLE 2

Mean area under the curve of the thickness of the outer nuclear layer

| Treatment | Thickness of the outer nuclear layer (AUC, µm × mm, mean of both eyes ± standard deviation) |
|---|---|
| EFX 12.5 mg/kg | 170 ± 72 (p = 0.04 comparing to vehicle group) |
| EFX 25 mg/kg | 200 ± 73 (p = 0.0002 comparing to vehicle group) |
| EFX 50 mg/kg | 172 ± 61 (p = 0.035 comparing to vehicle group) |
| Vehicle | 116 ± 51 |
| NaCl 0.9% | 91 ± 59 |
| PBN 50 mg/kg | 247 ± 44 (p < 0.0001 comparing to NaCl 0.9% group) |
| Non induced Rats (n = 5) | 274 ± 18.83 |

In contrast to the 0.9% NaCl solution (negative control), PBN (positive control) protects the outer nuclear layer from damages or degenerations induced by the blue light, as shown by the comparison with the non-induced rats, which validates the experimental procedure. It is furthermore observed that the upper hemisphere (from 0 to +4 mm) is more damaged than the lower hemisphere (from −4 to 0 mm). In addition, no difference is found between the vehicle and 0.9% NaCl groups.

Regarding etifoxine, regardless of the dose, the latter protects significantly, as compared to the vehicle, the outer nuclear layer from damages or degenerations induced by blue light.

In conclusion, etifoxine protects retinal photoreceptors from damages or degenerations induced by blue light, which indicates a protective effect of this compound regarding retinal degeneration and/or light-induced retinal damage, such as age-related macular degeneration (AMD).

The invention claimed is:

1. A method for the treatment of a light-induced damage and/or degeneration of the retina in an individual, comprising administering the individual with an effective amount of a compound of the following formula (I):

wherein:
a represents 0 or 1,
b represents a single bond or a double bond,
c represents a single bond or a double bond,
d represents 0 or 1,
X represents an oxygen or nitrogen atom, provided that when X represents an oxygen atom then d has the value of 0 and when X represents a nitrogen atom then d has the value of 1,
$R_1$, $R_2$, $R_3$, and $R_4$, which are the same or different, represent a hydrogen atom, a halogen atom, in particular selected from F, Cl, Br, or I, a hydroxyl group, or an alkoxyl group having 1 or 2 carbon atoms,
$R_5$ and $R_6$, which are the same or different, represent a hydrogen atom, an alkyl or cycloalkyl group having from 1 to 6 carbon atoms, or an aryl group having 6 carbon atoms in which the aromatic ring may be substituted by one or more halogen atoms or one or more hydroxyl groups, alkoxyl groups having 1 or 2 carbon atoms, trifluoromethyl groups or nitro groups,
$R_7$ represents a hydrogen atom, a hydroxyl group, or an alkyl or hydroxyalkyl group having from 1 to 3 carbon atoms,
$R_8$ represents an oxygen atom or a -$NR_9R_{10}$ group, $R_9$ and $R_{10}$, which are the same or different, representing a hydrogen atom, a hydroxyl group, or an alkyl or hydroxyalkyl group having from 1 to 3 carbon atoms, provided than when $R_8$ represents an oxygen atom then a has the value 1, b represents a single bond and c represents a double bond and that when $R_8$ represents a -$NR_9R_{10}$ group then a has the value 0, b represents a double bond and c represents a single bond,
or a pharmaceutically acceptable salt thereof.

2. The method of claim 1, wherein formula (I) is represented by the following formula (II):

(II)

wherein $R_1$, $R_2$, $R_3$, $R_4$, $R_5$, $R_6$, $R_9$ and $R_{10}$ are as defined above.

3. The method of claim 1, wherein formula (I) is represented by one of the following formula (IIa), (IIIb) or (IV):

(IIIa)

(IIIb)

(IV)

4. The method of claim 1, wherein formula (I) is represented by the following formula (V):

(V)

wherein $R_1$, $R_2$, $R_3$, $R_5$, $R_6$, and $R_7$ are as defined in claim 1.

5. The method of claim 1, wherein formula (I) is represented by the following formula (VI) or (VII):

(VI)

(VII)

6. The method of claim 1, wherein the compound or pharmaceutically acceptable salt thereof is administered in a unit dose of 50 mg to 1500 mg.

7. The method of claim 1, wherein the compound or pharmaceutically acceptable salt thereof is administered by the oral route.

8. The method of claim 1, wherein the compound or pharmaceutically acceptable salt thereof in the form of a powder, tablets, capsules or sachets.

9. The method of claim 1, for the treatment of photoretinitis, retinitis pigmentosa, age-related maculopathy (ARM), or age-related macular degeneration (AMD).

10. The method of claim 1, wherein the compound of formula (I) or pharmaceutically acceptable salt thereof is in combination with at least one additional compound useful for treating a light-induced damage and/or a degeneration of the retina selected from the group consisting of an anti-VEGF, a corticoid and an antioxidant.

11. The method of claim 1, wherein the individual is treated with dynamic phototherapy.

12. A pharmaceutical composition comprising as active ingredients
at least one compound of the following formula (I), (I)

wherein:
a represents 0 or 1,
b represents a single bond or a double bond,
c represents a single bond or a double bond,
d represents 0 or 1,
X represents an oxygen or nitrogen atom, provided that when X represents an oxygen atom then d has the value of 0 and when X represents a nitrogen atom then d has the value of 1,
$R_1$, $R_2$, $R_3$, and $R_4$, which are the same or different, represent a hydrogen atom, a halogen atom, in particular selected from F, Cl, Br, or I, a hydroxyl group, or an alkoxyl group having 1 or 2 carbon atoms, $R_5$ and $R_6$, which are the same or different, represent a hydrogen atom, an alkyl or cycloalkyl group having from 1 to 6 carbon atoms, or an aryl group having 6 carbon atoms in which the aromatic ring may be substituted by one or more halogen atoms or one or more hydroxyl groups, alkoxyl groups having 1 or 2 carbon atoms, trifluoromethyl groups or nitro groups, $R_7$ represents a hydrogen atom, a hydroxyl group, or an alkyl or hydroxyalkyl group having from 1 to 3 carbon atoms,

$R_8$ represents an oxygen atom or a -$NR_9R_{10}$ group, $R_9$ and $R_{10}$, which are the same or different, representing a hydrogen atom, a hydroxyl group, or an alkyl or hydroxyalkyl group having from 1 to 3 carbon atoms, provided than when $R_8$ represents an oxygen atom then a has the value 1, b represents a single bond and c represents a double bond and that when $R_8$ represents a -$NR_9R_{10}$ group then a has the value 0, b represents a double bond and c represents a single bond, or a pharmaceutically acceptable salt thereof, and at least one additional compound useful for the treatment of a light-induced damage and/or a degeneration of the retina selected from the group consisting of an anti-VEGF, a corticoid, and an antioxident, optionally in association with a pharmaceutically acceptable vehicle.

13. The pharmaceutical composition of claim 12, wherein formula (I) is represented by one of the following formula (IIIa), (IIIb), (IV), (VI) or (VII):

(IIIa)

(IIIb)

(IV)

(VI)

(VII)

* * * * *

UNITED STATES PATENT AND TRADEMARK OFFICE
CERTIFICATE OF CORRECTION

PATENT NO. : 9,872,858 B2  
APPLICATION NO. : 15/115089  
DATED : January 23, 2018  
INVENTOR(S) : Verleye et al.

Page 1 of 1

It is certified that error appears in the above-identified patent and that said Letters Patent is hereby corrected as shown below:

In the Claims

Column 16, Claim 1, Line 67:  
Please change:  
"provided than when $R_8$ represents an oxygen atom then"  
To:  
- provided that when $R_8$ represents an oxygen atom then -

Column 19, Claim 12, Line 17:  
Please change:  
"atoms, provided than when $R_8$ represents an oxygen"  
To:  
- atoms, provided that when $R_8$ represents an oxygen -

Column 19, Claim 12, Line 27:  
Please change:  
"VEGF, a corticoid, and an antioxident,"  
To:  
- VEGF, a corticoid, and an antioxidant, -

Signed and Sealed this  
Nineteenth Day of June, 2018

Andrei Iancu  
*Director of the United States Patent and Trademark Office*